(12) United States Patent
Daft et al.

(10) Patent No.: US 8,647,279 B2
(45) Date of Patent: Feb. 11, 2014

(54) VOLUME MECHANICAL TRANSDUCER FOR MEDICAL DIAGNOSTIC ULTRASOUND

(75) Inventors: Christopher M. Daft, Dublin, CA (US); Paul A. Wagner, San Carlos, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 612 days.

(21) Appl. No.: 12/813,413

(22) Filed: Jun. 10, 2010

(65) Prior Publication Data

US 2011/0306886 A1    Dec. 15, 2011

(51) Int. Cl.
*A61B 8/00* (2006.01)

(52) U.S. Cl.
USPC .......................................... 600/459; 600/443

(58) Field of Classification Search
USPC .................. 600/443–449, 459; 310/334–337
See application file for complete search history.

(56) References Cited

U.S. PATENT DOCUMENTS

| | | | | |
|---|---|---|---|---|
| 5,471,988 A * | 12/1995 | Fujio et al. | | 600/439 |
| 5,490,512 A * | 2/1996 | Kwon et al. | | 600/447 |
| 5,575,290 A * | 11/1996 | Teo et al. | | 600/456 |
| 5,902,242 A * | 5/1999 | Ustuner et al. | | 600/443 |
| 6,132,375 A | 10/2000 | Napolitano | | |
| 6,142,946 A * | 11/2000 | Hwang et al. | | 600/459 |
| 6,540,681 B1 | 4/2003 | Cheng et al. | | |
| 6,582,367 B1 * | 6/2003 | Robinson et al. | | 600/443 |
| 7,466,256 B2 | 12/2008 | Brueske et al. | | |
| 7,583,214 B2 | 9/2009 | Liu et al. | | |
| 7,691,060 B2 * | 4/2010 | Angelsen et al. | | 600/443 |
| 7,750,537 B2 * | 7/2010 | Hossack et al. | | 310/334 |
| 8,038,619 B2 * | 10/2011 | Steinbacher | | 600/444 |
| 2003/0097068 A1 * | 5/2003 | Hossack et al. | | 600/443 |
| 2004/0186381 A1 * | 9/2004 | Ma et al. | | 600/454 |
| 2005/0124889 A1 * | 6/2005 | Flesch | | 600/445 |
| 2006/0241453 A1 * | 10/2006 | Nguyen-Dinh et al. | | 600/445 |
| 2007/0242567 A1 | 10/2007 | Daft et al. | | |
| 2009/0079299 A1 | 3/2009 | Bradley et al. | | |
| 2010/0063397 A1 * | 3/2010 | Wagner | | 600/459 |
| 2011/0060255 A1 * | 3/2011 | Chen | | 601/2 |

* cited by examiner

*Primary Examiner* — Long V. Le
*Assistant Examiner* — Lawrence Laryea

(57) ABSTRACT

A one-dimensional array is used for transmit operation, allowing connection with an imaging system for planar scanning and avoiding transmit electronics in the transducer array. A multi-dimensional array is used for reception only, avoiding transmit interconnects while providing greater coherence in elevation. Both arrays are moved to scan different planes, allowing acquisition of data representing a volume. This transducer arrangement may be used for scanning breasts for cancer screening.

20 Claims, 5 Drawing Sheets

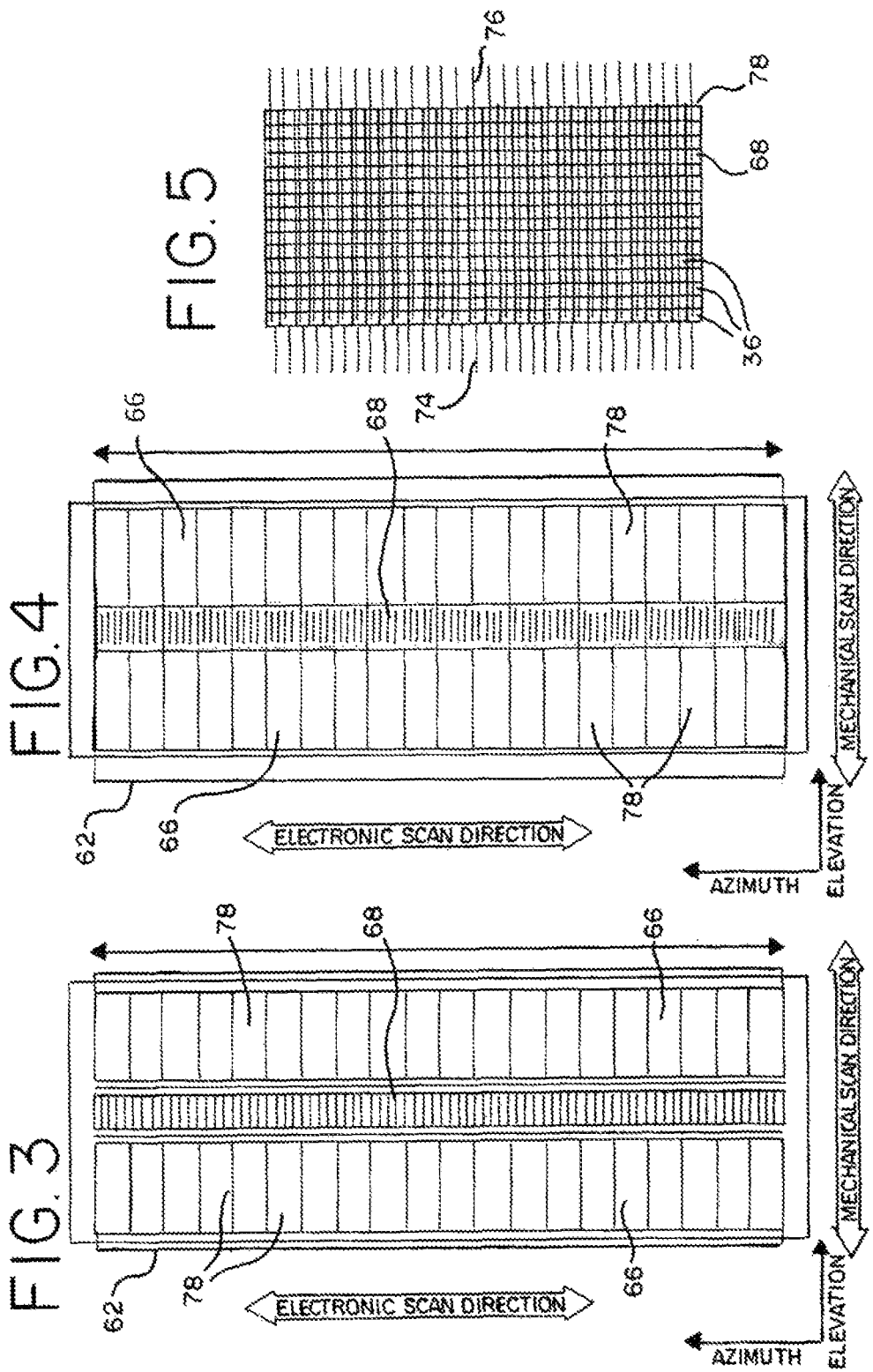

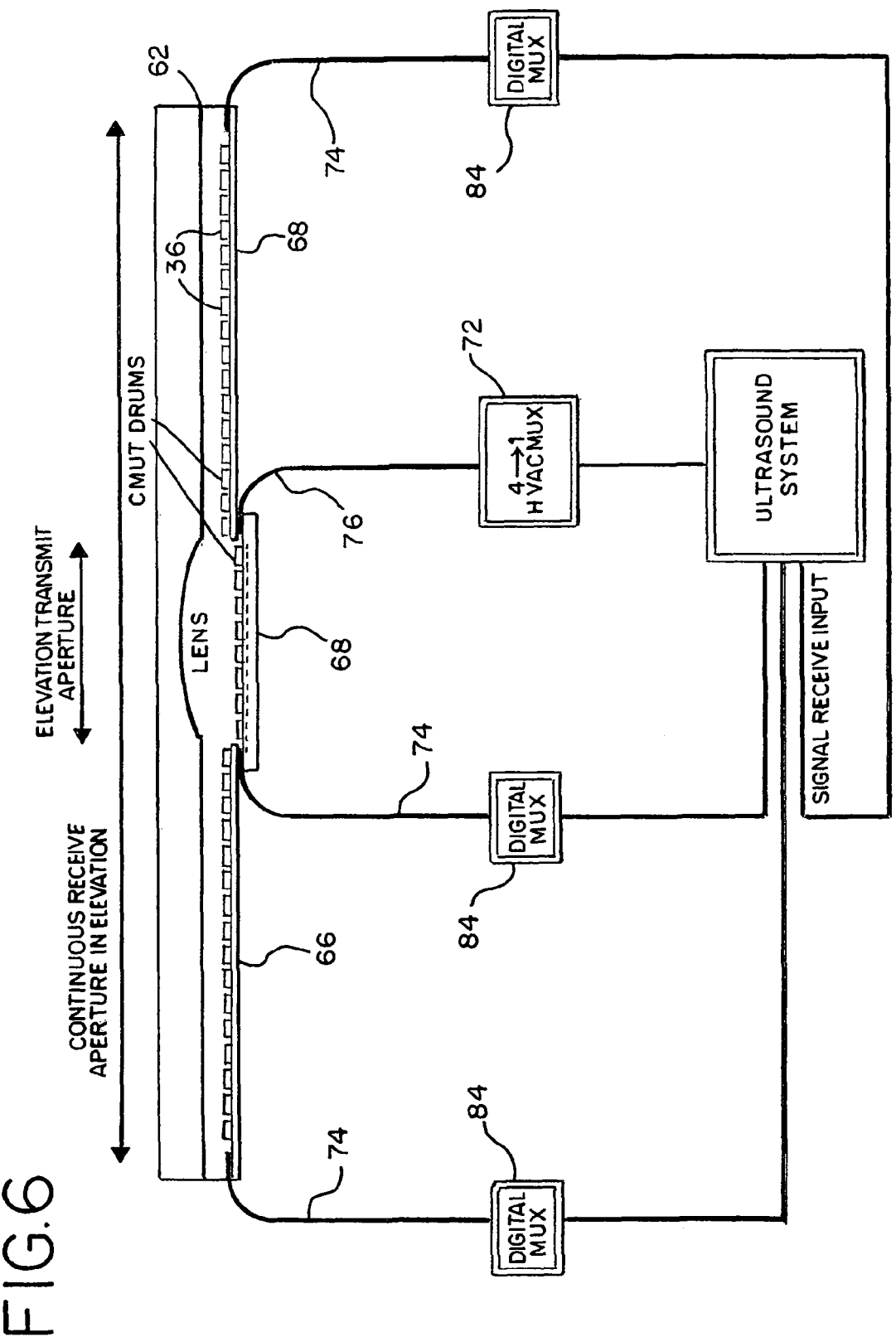

FIG. 10
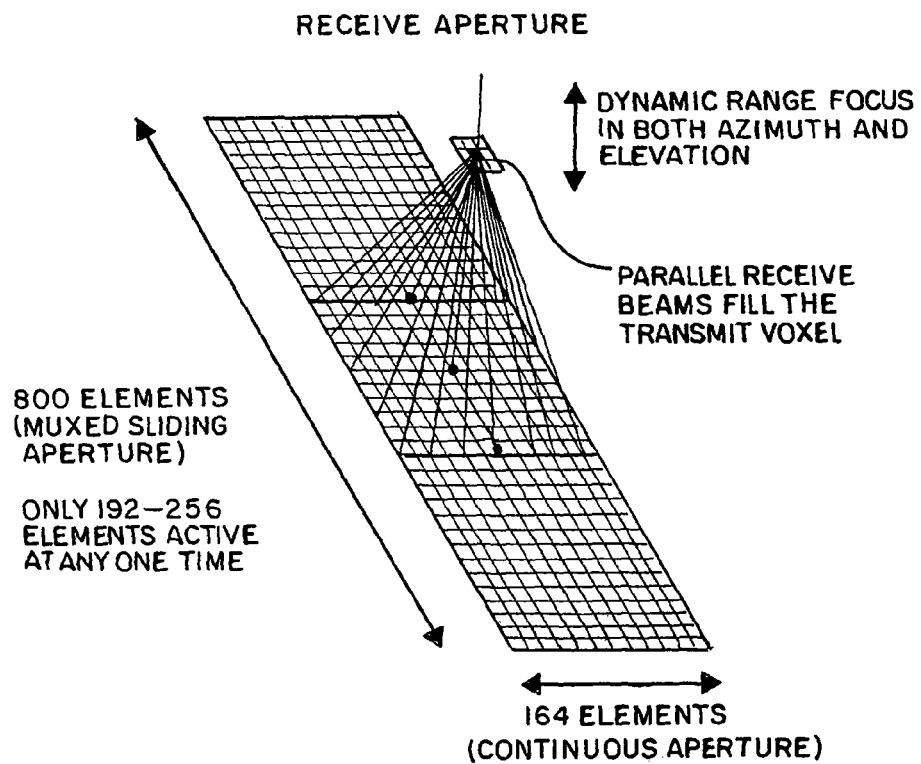
RECEIVE APERTURE
DYNAMIC RANGE FOCUS IN BOTH AZIMUTH AND ELEVATION
PARALLEL RECEIVE BEAMS FILL THE TRANSMIT VOXEL
800 ELEMENTS (MUXED SLIDING APERTURE)
ONLY 192-256 ELEMENTS ACTIVE AT ANY ONE TIME
164 ELEMENTS (CONTINUOUS APERTURE)
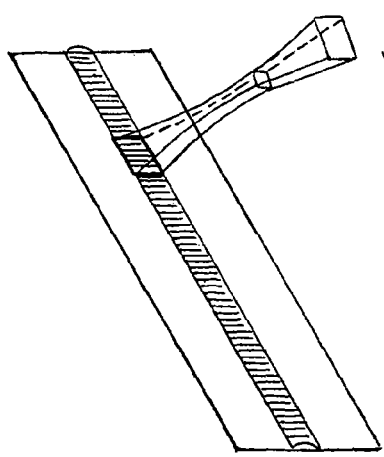
FIG. 11A
35° TRANSMIT
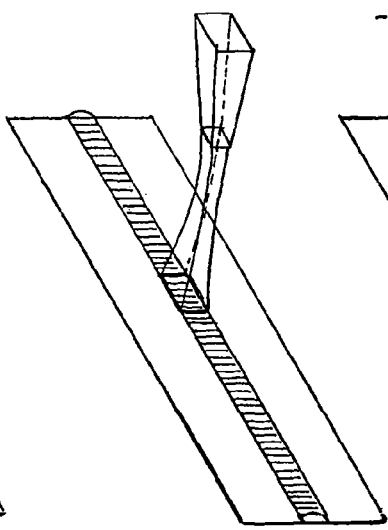
FIG. 11B
0° TRANSMIT
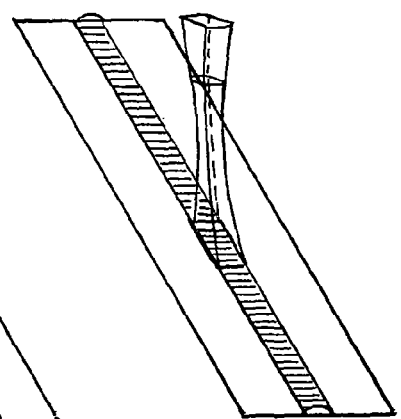
FIG. 11C
-35° TRANSMIT

VOLUME MECHANICAL TRANSDUCER FOR MEDICAL DIAGNOSTIC ULTRASOUND

BACKGROUND

The present embodiments relate to ultrasound transducers. In particular, the present embodiments relate to volume mechanical transducers.

Wobblers are one-dimensional arrays used for scanning a volume. The one-dimensional array is rotated or translated mechanically. Planar scans are performed at different positions of the array. For both transmission and reception, a beamformer with only sufficient channels for a planar scan may be used for acquiring data representing a volume. However, the one-dimensional array may have limited resolution due to fixed focus in elevation.

Other than a wobbler, a breast scanning transducer may include a one-dimensional array mechanically moved to scan a breast. Like the wobbler, the elevation resolution may be less than desired, such as for potentially detecting both low-contrast lesions and micro-calcifications. To detect such lesions and micro-calcifications, the transducer aperture size and coherence are increased, and the element size is decreased.

A fully populated matrix transducer (e.g., two-dimensional array) may increase aperture size and coherence with decreased element size. However, the number of elements greatly increases, resulting in either power dissipating or heat generating transmit electronics in the transducer or an imaging system with a large number of channels. This problem is compounded by each element being used for both transmit and receive operation. The interconnect requirements for fine-pitch transmit and receive elements may be difficult to provide.

BRIEF SUMMARY

The present invention is defined by the following claims, and nothing in this section should be taken as a limitation on those claims. By way of introduction, the preferred embodiments described below include methods, transducer arrays, and systems for medical diagnostic ultrasound imaging. A one-dimensional array is used for transmit operation, allowing connection with an imaging system for planar scanning and avoiding matrix transmit electronics in the transducer array. A multi-dimensional array is used for reception only, avoiding transmit interconnects while providing greater coherence in elevation. Both arrays are moved to scan different planes, allowing acquisition of data representing a volume. In one embodiment, this transducer arrangement is used for scanning breasts for cancer screening.

In a first aspect, a transducer array is provided for medical diagnostic ultrasound imaging. A one-dimensional transducer array is configured for transmit only operation or transmit and receive operation. The one-dimensional transducer array has, for transmit operation, a plurality of transmit elements distributed along an azimuth dimension with only a single row of the elements in an elevation dimension. A multi-dimensional transducer array is adjacent an elevation edge of the one-dimensional transducer array. The multi-dimensional transducer array is configured for receive only operation. The multi-dimensional transducer array has N×M receive elements distributed along the azimuth and elevation dimensions where N and M are both greater than one. A motor is configured to move the one-dimensional and multi-dimensional transducer array together along the elevation direction.

In a second aspect, an ultrasound system is provided for medical diagnostic ultrasound imaging. A transducer array includes a two-dimensional transducer array having a first row of elements configured for transmit operation and at least second and third rows of elements configured for receive only operation. A guide is arranged to translate the transducer array generally perpendicular to the first row. A beamformer is configured to transmit acoustic energy with the first row of elements and receive echo signals with the second and third rows of elements. The transmit and receive are repeated with the transducer array at different positions along the guide such that a volume is scanned.

In a third aspect, a method is provided for medical diagnostic ultrasound imaging. A plurality of transmit beams are transmitted in a plane with a one-dimensional array. In response to the transmitting, receive beams are received in the plane with a multi-dimensional array. The multi-dimensional array abuts the one-dimensional array and is free of connection with a transmit beamformer. The one-dimensional array and the multi-dimensional array are mechanically moved. The transmitting and receiving are repeated at different positions of the one and multi-dimensional arrays.

Any one or combinations of any two or more of the aspects discussed above may be used. Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

FIG. 3 shows one embodiment of a multi-dimensional transducer array;

FIG. 4 shows another embodiment of a multi-dimensional transducer array;

FIG. 5 shows an example one-dimensional transmit array also operable as a multi-dimensional receive array;

FIG. 6 is a cross-section view of one embodiment of the multi-dimensional transducer array of FIG. 4;

FIG. 10 is an example illustration of receive scanning in an azimuth plane; and

FIGS. 11A-C show examples of transmitting at different angles.

DETAILED DESCRIPTION OF THE PREFERRED EMBODIMENTS

Rather than dealing with interconnects for transmit and reception using a full matrix or two-dimensional array, a simpler solution may be a traditional one-dimensional (PZT or cMUT) transmit transducer driven by the imager's electronics. The one-dimensional transmit transducer is flanked by one or two banks of finely-sampled receive-only arrays.

The one-dimensional transmit aperture may be only used for transmit in one embodiment (see FIG. 3) or may also be configured to function as a matrix of receive elements in another embodiment (see FIG. 4). Two multi-dimensional cMUT arrays supply a large aperture, elevation coherence and small elements. For scanning a breast, the transmit elevation aperture may be increased by synthesis across several firings, if, for example, an elevation focus lens is used.

An ultrasound system includes a multi-dimensional transducer. The transducer is formed from a plurality of transducers or arrays. A one-dimensional array is used for transmit-only or transmit-receive functions. One or more multi-dimensional (e.g., 2D) arrays are used for receive-only functions. The multi-dimensional transducer array matrices abut either side of the transmitting transducer. The transducer arrays are translated perpendicular to the one-dimensional transmit array, allowing transmit aperture synthesis. The one-dimensional array may be serviced by the imaging system, avoiding transmit electronics in the probe. The receive-only array matrices may be cMUTs monolithically integrated above partial beamforming electronics or other combination circuits to reduce the number of receive beamformer channels needed in the imaging system.

Figure 1:
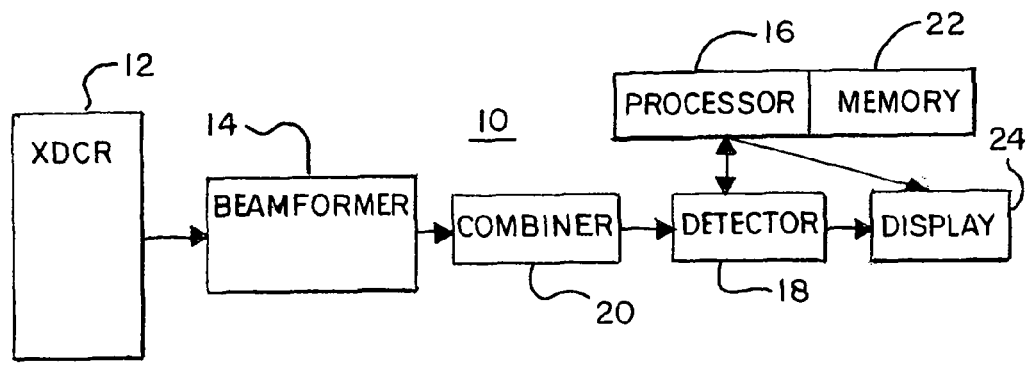
FIG. 1 is a block diagram of one embodiment of a system for scanning with ultrasound.

FIG. 1 shows a system 10 for medical diagnostic ultrasound imaging. The system 10 includes a transducer probe 12, a beamformer 14, a processor 16, a detector 18, a combiner 20, a memory 22, and a display 24. Additional, different, or fewer components may be provided. For example, the system 10 includes a user interface. In one embodiment, the system 10 is a medical diagnostic ultrasound imaging system. In other embodiments, the processor 16 and/or memory 22 are part of a workstation or computer different or separate from an ultrasound imaging system. The workstation is adjacent to or remote from the ultrasound imaging system. In some embodiments, the transducer probe 12 is provided without other components.

In one embodiment, the system represents an automated breast volume scanner. The transducer probe 12 is provided for scanning the breast. The transducer probe 12 is handheld or may be part of an automated scanning system. For example, the transducer probe 12 is supported by a robotic arm or a support arm. Gravity, servos, motors, springs, hydraulics or other mechanism hold the transducer probe 12 in place against a patient's breast. Other applications than breast imaging may be provided.

The transducer probe 12 is a transducer array for medical diagnostic ultrasound imaging. The transducer probe 12 may be used with the system of FIG. 1 or a different system. The transducer probe 12 includes a probe housing 60, a transducer array 62, and a guide 64 (see FIG. 2). Additional, different, or fewer components may be provided, such as a cable and/or electronics.

The transducer probe 12 includes a planar array, a curved array, a two-dimensional array, a radial array, an annular array, or other multidimensional array of transducer elements. For example, the transducer probe 12 includes a multi- or two-dimensional array. A two-dimensional array has elements spaced in multiple directions but does not necessarily have an equal extent in each direction. Multi-dimensional arrays include 1.25D, 1.5D, 1.75D, annular, radial, or other arrangements of elements over an area rather than a line.

Figure 2:
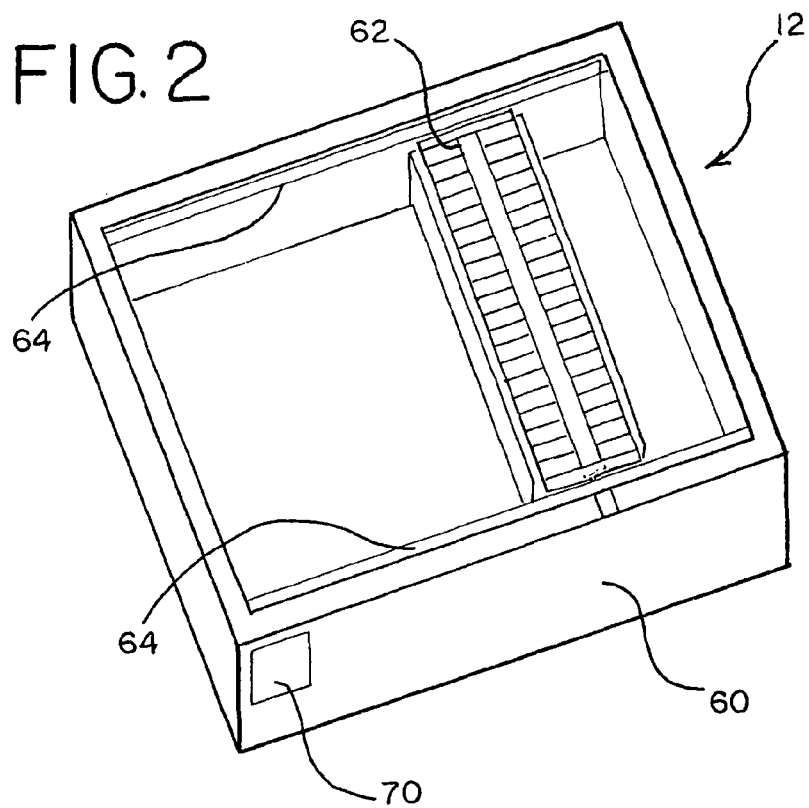
FIG. 2 is a perspective view of a breast transducer according to one embodiment.

Referring to FIG. 2, the transducer probe 12 includes a probe housing 60. For the breast imager, the probe housing 60 is a pod or outer shell of plastic, fiberglass, metal, and/or other material. An acoustic window, such as a flexible pad with or without gel or other ultrasound transmissive substance between the transducer array 62 and the pad, is provided. For example, the pad conforms to the shape of a compressed breast. Gel between the pad and the transducer array 62 allows the adaption and provides an acoustic path from the transducer array 62 to the breast. Alternatively, the probe housing 60 is part of a mammogram system or any other breast compression or scanning system.

In alternative embodiments for use scanning the breast or for other uses, the probe housing 60 is for handheld use. The shape and surface texture of the probe housing 60 includes a grip or handle for manual movement of the probe housing 60. An acoustic window, such as plastic or lens, may be provided. In yet other embodiments, the probe housing 60 is adapted in size, shape, material, and/or texture for use within the patient.

The probe housing 60 encases, surrounds most of, or is a protective frame work around the transducer array 62. The probe housing 60 may include handles, grips, latches, connections, a transducer cable, or other components. Electronics may be provided within the probe housing 60, but the probe housing 60 may be free of active (e.g., transistors, switches, or preamplifiers) electronics.

The transducer array 62 is a two-dimensional (multi-dimensional) transducer array. Two-dimensional is used in the context of separately addressable elements in azimuth and elevation. For example, N×M elements are provided with both N and M greater than one. M and N may be equal or unequal.

Examples of the two-dimensional transducer array 62 are shown in FIGS. 3 and 4. The transducer array 62 has at least two parts or groups of elements. In one embodiment, the two groups of elements are different rows or columns, but may be grouped in other ways. The difference in the groups is the operation and associated structure, such as connections with the beamformer 14. In the examples of FIGS. 3 and 4, the one row 68 of elements is configured for transmit operation, and one or more other rows 66 of elements are configured for only receiving. In other embodiments, more than one row may be used for transmission. The traces, connections, switches or switching used during scanning for a given imaging session may determine the use or configuration of the elements. The transmit and receive operation are physically collocated in the center region of the array 62, but may not have collocated centers.

The face of the transducer array 62 is planar, curved, concave, convex or other surface shape. The elements of the array 62 may be a single layer of acoustic elements or may include multiple layers of acoustic elements. The acoustic elements are transducer elements for transducing between electrical and acoustic energies.

The acoustic elements of the transducer probe 12 are lead zirconate titanate (PZT) piezoelectric transduction material, ferroelectric relaxor or PVDF materials, capacitive membrane ultrasonic transducer (cMUT) materials, micro-machined membranes or beams, microelectromechanical devices, other piezoelectric material, or other means for acoustic-to-electric and/or electric-to-acoustic transduction. For example, the acoustic elements are cMUT or micromachined structures, such as at least one flexible membrane suspended over a gap with electrodes on each side of the gap for transducing between acoustic and electrical energies. Each acoustic element is formed from one or more, such as 4-8, tens or other numbers of membranes and gaps (i.e., "drums" or cMUT cells). The electrodes of each of the membranes and gaps for a given element are connected in common to form the single acoustic element.

All of the acoustic elements comprise a same type of material, but multiple types of acoustic transducer materials may be used for different acoustic elements. The acoustic elements have one of various possible shapes, such as triangular, rectangular, square, polygonal, hexagonal, circular, irregular, or any combination of shapes on the face of the acoustic element (i.e., portion of the element placed adjacent a volume to be scanned).

The transducer probe 12 converts between electrical signals and acoustic energy for scanning a region of the patient's body. The region of the body scanned is a function of the type of transducer array 62 and position of the transducer probe 12 relative to the patient. A linear aperture may scan a rectangular or square, planar region of the body. As another example, a curved linear aperture may scan a pie shaped region of the body. Scans conforming to other geometrical regions or shapes within the body may be used, such as Vector™ scans. The scans are of a two-dimensional plane, such as scanning at different azimuth angles relative to the aperture. Different planes or different segments of a plane may be scanned by moving the transducer array 62. To scan a breast volume, the transducer array 62 is also or instead moved mechanically to scan different elevation spaced planes.

The row 68 of elements for transmit operation is a one-dimensional transmit array. Any number or size of elements may be provided. For example, the row 68 includes tens or hundreds of elements (e.g., 800 elements). The elements are the same or different size than elements of the other rows 66. The row 68 includes a number of elements operable with a two-dimensional scanning system, such as the beamformer 14 outputting 64, 128, 256 or other number of analog transmit waveforms for corresponding elements. For example, the elements transduce electrical energy provided by high voltage (e.g., 50, 100 or 200 volts) transmitters in the beamformer 14 of the imaging system. Transmit waveform generators are not provided in the transducer probe 12, but may be in alternative embodiments.

Where more elements are provided than transmit beamformer channels, the transducer probe 12 may include a multiplexer 72 (see FIG. 6). The multiplexer 72 selects an aperture of continuous or not continuous elements. For example, the multiplexer 72 creates a sliding or moving aperture for scanning the same plane at different times or for scanning a selected portion of the patient. In one embodiment, the transmit area formed by the faces of the transmit elements are 0.5 cm by 15 cm, but smaller or larger arrays may be provided.

In one embodiment, the elements for transmission of acoustic energy are configured for only transmit operation. For example, the row 68 is a transmit only array as shown in FIG. 3. The elements are connected to the transmit beamformer 14, but not connected to the receive beamformer 14 for acquiring responsive echoes. The transducer array 62 is fully bistatic through switching selection or fixed connections. In one embodiment of a transmit only row 68 of elements, the elements are PZT elements, but other types of elements may be used.

Where the row 68 of transmit elements is a one-dimensional array, a lens may be provided. Any lens material may be used, such as RTV. The lens is stacked above the face of the elements of the row 68. The lens provides a mechanical focus in elevation, such as a focal region around 15-20 mm of depth. Other focal depths may be used. In other embodiments, a lens with no focus or no lens is provided.

In other embodiments, the elements for transmission of acoustic energy are configurable for both transmit and receive operation. In the embodiments shown in FIGS. 4-6, the row 68 is used for both transmit and receive. The one-dimensional array of transmit elements is formed from a multi-dimensional array of receive elements. For transmit operation, the elements in the same column (elevation spaced elements) are connected together, such as by switches, creating a one-dimensional transmit array.

Alternatively, the electrode configuration defines the size of the transmit and receive elements as shown in FIG. 5. The row 68 includes acoustic elements 36 distributed along the azimuth and elevation dimensions. The elements 36 are separated from each other by kerfs and/or are separately electrically addressable, at least for receive operation. Each element 36 has top and bottom electrodes. The acoustic elements are individually accessed electrically with the bottom electrodes for the receive operation. For example, a flexible circuit material or flex 74 includes traces separately connecting with electronics and/or acoustic elements 36 for receive operation. The top electrodes extend across columns of the acoustic elements 36 in elevation. The top electrodes are common to a plurality of kerf separated, acoustic elements 36. The top electrodes form the transmit elements for transmit operation. The transmit elements connect to the flexible circuit material or flex 76. Each transmit element includes a plurality of receive elements. The transmit beamformer connects with the top electrode, and the receive beamformer connects with the bottom electrodes, allowing the same acoustic elements to have different transmit and receive element configurations. In other embodiments, the bottom electrodes define the transmit elements and the top electrodes define the receive elements.

Where the elements are cMUTs, bias voltage may be applied to the top or bottom electrodes. In one embodiment, the fixed DC bias is applied to the top electrodes.

The transmit flex 76 connects the transmit elements with the beamformer 14. The traces of the flex 76 may connect with coaxial cables. The cables connect the transducer probe 12 to the imaging system, spacing the transmit elements from the imaging system. The coaxial cables may terminate at a transducer connector of a transducer assembly. The transducer connector mates with a connector of the imaging system. This connection may be releasable. For example, the transducer probe 12 may be detached and reattached to the imaging system. When attached, the transmit flex 76 from the transducer probe 12 connects with the channels of the beamformer 14. Permanent connection may be provided. The transducer assembly is free of transmit electronics, such as the probe housing 60, the cable, and the transducer connector not having waveform generators. The imaging system provides the multi-level, high voltage waveforms.

As an alternative to the use of top and bottom electrodes, the row 68 is configured for transmit and receive operation by a transmit/receive multiplexer or switch. The same coaxial cables connect to the elements, but the transmit/receive multiplexer protects the receive beamformer 14 from the high voltage transmit waveforms.

In one embodiment shown in FIG. 4, the row 68 is tiled from a plurality of substrates. The elements 36 are provided on a tile, such as tiles with 24×80 acoustic elements 36. FIG. 5 represents one tile. By lapping or otherwise forming the elements 36 immediately adjacent at least the azimuth ends, the tiles may be placed adjacent to each other with minimal or no gap between the elements 36 from tile to tile.

The rows 66 operate in a receive only mode. Two rows 66 are shown, but one or more than two rows 66 may be provided. Each row 66 include receive elements 36. In one embodiment, each row 66 is a multi-dimensional transducer array of elements 36. The multi-dimensional transducer array has N×M receive elements 36 distributed along the azimuth and elevation dimensions where N and M are both greater than one. The array sampling pattern or relative placement of one acoustic element 36 to another acoustic element 36 is based on any sampling method, such as a triangular grid, rectangular grid, hexagonal grid, irregular grid, or random grid. Various spacing may be provided, such as ½ or one wavelength spacing between the centers of adjacent elements. The face or surface of the rows 66 is square, rectangular, triangular, hexagonal, irregular, or other shape. Any of various possible multi-dimensional arrangements of acoustic elements 36 may be used for the rows 66.

Figure 7:
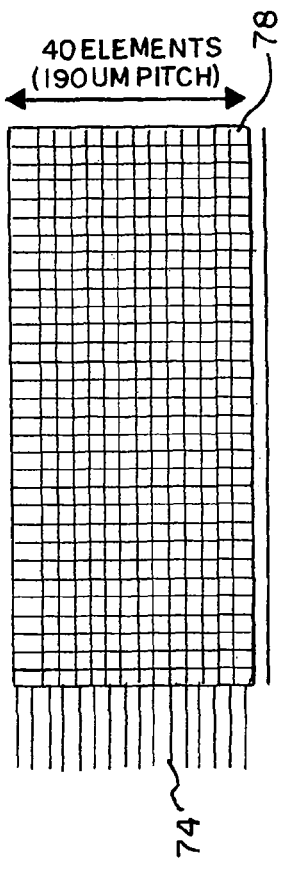
FIG. 7 illustrates a tile of a multi-dimensional receive array in one embodiment.
Figure 8:
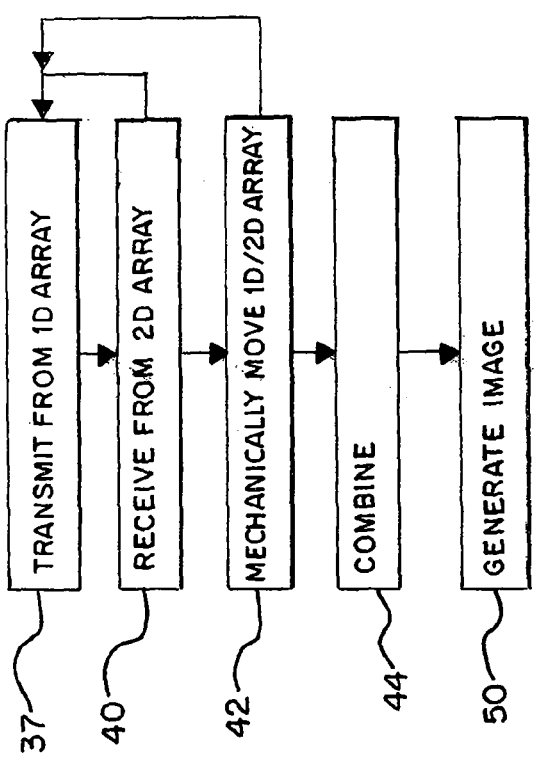
FIG. 8 is a flow chart diagram of one embodiment of a method for scanning with ultrasound.

In one embodiment, the rows 66 are arrays of cMUT elements. The arrays may be tiled as shown in FIGS. 3 and 4 where each tile includes a plurality of receive elements 36. FIG. 7 shows an example tile. Any size tile may be used. The rows 66 are formed from a plurality of tiles 78. The tiles 78 and positioning are the same as described for FIG. 5, but without the electrodes being used to define different sized transmit elements. In alternative embodiments, each row 66 is formed on a single substrate or by a single array. In the examples of FIGS. 3 and 4, the tiles are about 2 cm wide in elevation and 15 cm long in azimuth, but other sizes may be used. For example, the azimuth extent for both rows 66, 68 is at least about 10 centimeters, but may be more or less.

The gaps between the tiles are minimized, such as by forming the elements 36 against an edge of the tile or lapping the tile to position the elements at the edge. Minimizing the gaps may allow coherent beamformation across the entire 3.5 cm in the short axis dimension and across a sliding 4 cm or other sized aperture in the orthogonal dimension.

In one embodiment, the tile 78 or row 66 includes receive electronics. The receive electronics are a partial beamformer, multiplexer, or other circuit for reducing the number of channels. For example, the acoustic elements 36 are grouped into 2×2 or other size subapertures of adjacent elements 36. For each sub-aperture, a fixed analog phase shift between the elements is applied and the resulting signals summed or combined. This reduces the channel count by a factor of four. These sub-aperture signals are then partially beamformed, such as applying dynamic delays or phase shifts for 3×3 or other sized groups of elements or sub-apertures (e.g., 3×3 groups of 2×2 sub-apertures). This reduces the number of channels by a factor of nine. For example, 2800 elements are provided, but only 80 output lines are used where each output line is a signal partially beamformed from elements 36. Other partial beamformation or signal combination may be used, such as partial beamforming with dynamic delay or phasing for each element or time division multiplexing without beamformation.

The electronics may be integrated on a same substrate as the acoustic elements 36, such as using semiconductor processing to make both the electronics and acoustic elements 36. In other embodiments, a separate substrate or board is provided for the electronics or the die may be connected by through-silicon vias, z-axis film or other vertical interconnect.

The bottom electrodes of the elements connect with the electronics, and the top electrodes connect with a bias source, such as a DC bias. The top electrodes may be a common electrode for the entire tile 78 or row 66.

FIG. 6 shows a short axis cross section of the transducer array 62 of FIG. 4. The rows 66 are adjacent to the row 68. The elevation edges of the row 68 are adjacent to the elevation edges of the rows 66. The transmit row 68 is positioned behind the substrate of the receive rows 66 to allow the acoustic elements 36 to be adjacent to each other even across the rows 66, 68. Alternatively, the rows 66, 68 are placed adjacent each other where the gap is minimized by machining the die, etching the die or forming the elements 36 immediately next to the edges.

The one-dimensional transmit array with or without the transmit elements also useable as a one or multi-dimensional receive array is connected together with the multi-dimensional receive array. The connection is through bonding, press fit, held by backing, or sharing a common frame. Other connections may be possible with or without intermediary layers or components. A gap may be provided between the rows 66, 68.

In the embodiment of FIG. 4 where the transmit elements are formed from groups of receive acoustic elements 36, the acoustic elements 36 of the different rows 66, 68 are the same size. The acoustic elements 36 of the transmit array in the row 68 are the same size as the elements in the multi-dimensional, receive only rows 66. In other embodiments, different size acoustic elements are provided. For example, the transmit only elements of FIG. 3 have at least a greater elevation extent and may have greater azimuth extent than the elements of the receive only arrays.

In one embodiment, the tiles 78 of the receive rows 66 have receive flex 74 extending from one side as shown in FIG. 4. For the transmit row 68, the receive flex 74 also extends from one side. The transmit flex 76 extends from the other side of the row 68. Since the tiles 78 of the receive rows 66 are only used for receive operation, transmit flex 76 is not provided as part of the configuration. Due to trace density, the flexes 74, 76 may be multi-layer flex.

In one embodiment represented by FIG. 6, the receive flex 74 connect with the tiles 78. Through the circuits in the tile 78, the flex 74 connects with the bottom electrodes of the elements 36. The transmit flex 76 connects with the top electrodes of the elements 36 in the transmit row 68. Other arrangements are possible.

If the electronics of the tiles 78 include analog-to-digital converters, such as between two sub-aperture circuits, the output may be digital. High speed serial interconnect such as LVDS or optical links may be used to decrease the number of interconnects. Alternatively, analog output is provided.

Where the array 62 is sufficiently large, one or more multiplexers 84 may be provided to select an aperture. The multiplexer selects the aperture in azimuth and/or elevation. The aperture is a sub-set of the acoustic elements 36, such as a 192, 256 or other number of columns of elements in azimuth. The aperture selected is the same or different for transmit and receive operation.

Where the row 68 includes a lens, the signals from the acoustic elements of the row 68 used for receive operation may be delayed to account for the lens delay.

Referring again to FIG. 2, the transducer array 62 connects with the guide 64. The guide 64 is a rail, a pulley, a hydraulic system, a screw drive, mechanical linkage, ball bearings, rack and pinion, or other mechanism for guiding the transducer array 62 in rotational or lateral movement. For example, the guide 64 includes two grooves where the transducer array 62 rests in the grooves and is connected to a pulley or chain. The grooves support both the one and multi-dimensional arrays 66, 68 of the transducer array 62 to move generally perpendicular to the rows 66, 68, such as in an elevation direction.

A motor 70 connects with the array 62, such as through a pulley. The motor 70 applies force to move the transducer array 62. Any speed of motion may be provided to translate or move the transducer array 62. The scan head is mechanically translated in the direction parallel to the short axis, causing the transmit plane to sweep across an entire volume. A controller operates the motor 70 at the desired times and/or speed. Any type of motor may be used, such as a stepper motor, electric motor, or pump.

The one-dimensional transmit array is used for transmit operation and a multi-dimensional receive array is used for receive operation. The beamformer 14 uses the transducer array 62. In one embodiment, the beamformer 14 outputs analog transmit waveforms and receives digital, partial beamformed data for scanning a plane. In other embodiments, analog signals are received and/or digital data is output. The beamformer 14 is a transmit beamformer, receive beamformer, combinations thereof, or other now known or later developed device for scanning a region with the transducer probe 12.

The beamformer 14 is configured by hardware and/or software. For example, focus tables are used to determine the delays or phases for steering acoustic beams. Pursuant to software control, the desired waveforms are generated for transmit operation, and the desired receive process is implemented.

In one embodiment, the beamformer 14 includes transmitters or waveform generators for generating electrical waveforms for each element of a transmit aperture. The waveforms are associated with phase and amplitude. The waveforms for a given transmit event may have the same or different phasing. The electrical waveforms are relatively weighted and delayed to form an acoustic beam with a desired phase and amplitude characteristic. For example, the transmit beamformer includes amplifiers, phase rotators, and/or controllers to generate sequential, steered pulses with the desired phase and amplitude in relation to other acoustic beams. Converging, diverging or planar beams may be used.

The transmit beamformer is part of an imaging system. For example, the transmit beamformer is separate from a transducer probe 12 or assembly. The imaging system, including the transmit beamformer, is releasably connectable with the transducer array. The transmit waveforms are output by the transmit beamformer to the transducer probe 12.

The transmit beamformer includes channels where a relatively delayed and/or apodized waveform is output on each channel. The waveforms are provided to the one-dimensional transmit array for scanning the plane with the row 68 of transmit elements. A different plane is scanned for different positions of the transducer array 62.

Multiple transmit apertures may be used for each plane, such as for a large azimuth extent array. The transmit beamformer scans sequentially using each aperture across the face of the transducer array 62.

The beamformer 14 may include receive beamformers, such as delays, phase rotators, amplifiers, and/or adders for relatively delaying and summing received signals to form one or more receive beams with dynamic focusing. For example, using shared processing, separate processing, or combinations thereof, a plurality (e.g., tens or hundreds) of parallel receive beamformers are provided to form a respective plurality of receive beams in response to a given transmit beam. Alternatively, the beamformer 14 includes a processor for Fourier or other analysis of received signals to generate samples representing different spatial locations of the scanned region. In other embodiments, only one or a few (e.g., nine or fewer) receive beams are generated for each transmit beam.

The receive beamformer connects with the receive elements of the transducer array 62 after pre-amplification, any signal conditioning (e.g., filtering) and analog-to-digital conversion. The receive beamformer may be on-chip with the receive elements. The transmit elements for a given transmit event may be a sub-set of the receive elements for a given aperture. In one embodiment, at least two rows 66 of multi-dimensional arrays of receive elements are used. Each row 66 may be separately beamformed in response to the same transmit beam or may be beamformed together as one array.

In one embodiment, the receive beamformer is in the imaging system. The receive beamformer may include a decoder or multiplexer for extracting data from the separate transducer probe 12, such as by reversing time multiplexed data. The transducer probe 12 is free of receive beamforming circuits.

In another embodiment, the transducer probe 12 includes a partial beamformer. The partial beamformer is adjacent to the transducer array 62, such as being within the probe housing 60, integrated in a same substrate as cMUT receive elements, or stacked with the transducer array 62.

Where partial beamforming is provided in the transducer probe, the imaging system includes the remainder of the beamformer. The remainder may be a system beamformer for scanning a plane. By partially beamforming in the transducer probe 12, a receive beamformer in the imaging system intended for scanning with a transmit one-dimensional array may be used to scan with a receive multi-dimensional array. The system beamformer applies delays and/or phase and relative amplitude weighting to form beams from the partially beamformed data.

In one embodiment, a cMUT array 62 is monolithically integrated above electronics in a silicon or other semiconductor substrate. The electronics are configured to reduce a number of signals from N×M signals by at least half through combination of the signals. The system beamformer further combines the signals.

The transducer probe 12 and beamformer 14 are connected together, such as the transmit beamformer channels connecting through coaxial cables to the transducer probe 12. The transducer probe 12 and beamformer 14 are configured to scan a planar region or a segment of a planar region. The beamformer 14 is controlled or programmed to perform the scan. The beamformer parameters, such as relative delays and/or phasing for focus, apodization, beam amplitude, beam phase, frequency, or others, are set. The aperture for transmit and the aperture for receive on the transducer probe 12 is set. The beamformer 14 and transducer probe 12 are used to generate the waveforms for the aperture and convert the waveforms to acoustic energy for transmitting the beam. The beamformer 14 and transducer probe 12 are used to receive acoustic energy at the receive aperture, convert the acoustic energy to electrical energy, and beamform the received electrical signals.

Electric steering may be used to scan a plane. A volume scan may be performed using mechanical movement of the transducer array 62. Any pattern or distribution of scan lines and/or apertures may be used. Acoustic energy is transmitted in any of various now known or later developed scan patterns along each scan plane for acquiring data. The scan plane is then altered to another location in the volume by moving the transducer array 62. By moving the transducer array 62 along the guide 64, a volume may be scanned. The volume is represented by data for a plurality of planes.

For each plane position, the beamformer 14 is configured to scan the plane once. Alternatively, the plane is scanned multiple times but with different scan line angles in azimuth for compounding spatially. Different aperture locations may be used for scanning a given location from different angles.

The aperture used for scanning may be shifted. For example, one aperture is used to scan one region of a plane and another aperture is used to scan another region of the plane.

For a given volume, the scans may be repeated. By repeating the scans, a sequence of frames of voxel data is obtained.

Each frame represents the entire three-dimensional scanned volume, but may only represent smaller regions within the volume, such as a plane. By repeating the scanning, a plurality of frames of beamformed data representing the volume and/or plane is acquired. Any of scan line, part of frame, frame, or group of frame interleaving may be used.

The combiner 20 is part of the beamformer 14, the detector 18, or separate. The combiner 20 is a memory, buffer, phase rotator, processor, adder, multipliers or other components for interpolating in-phase and quadrature or other signals with phase information or combining signals without phase information. As a coherent combiner, the combiner 20 is configured as hardware, with software, or combinations thereof to interpolate at least some of the data output by the beamformer 14. For example, one or more samples representing scan lines between received scan lines are interpolated. As another example, data for a scan line is replaced by interpolated data. The interpolated data is output to the detector 18. The detector 18 operates on interpolated data, actual received data, or combinations of both. In alternative embodiments, the combiner 20 is after the detector 18 for combining incoherent data. In yet other embodiments, combiner 20 is prior to detection for combining coherent data and after detection for combining incoherent data. Alternatively, no combiner 20 is provided.

The combiner 20 combines data from the same or different scans. For example, each row 66 of receive elements 36 is used to separately form beams in a same plane and in response to a same transmit beam. After detection, the beams are combined incoherently. For the embodiment of FIG. 3, incoherent compounding between the left and right blocks of receive tiles 78 may prevent or limit sidelobes observed in coherent beam formation due to the large hole in the receive aperture in the fully bistatic approach. No receiving is done on the 1D array in the center. For the embodiment of FIG. 4, a continuous receive aperture is available, so each receive beam is formed from all of the receive elements in the aperture.

As another example, the same plane is scanned two or more times, but from different angles in azimuth. The resulting data is combined coherently. Data from the same plane is combined coherently (i.e., with phase information) or incoherently (e.g., after detection).

Steered spatial compounding may be implemented in the long axis (e.g., azimuth) dimension to improve detection of low contrast lesions. 2-way steered spatial compounding in azimuth combined with dual angle 1-way steered spatial compounding in elevation may image low contrast lesions well. Alternatively, transmit aperture synthesis may be implemented along the long axis. Plane or other broad transmit waves are transmitted at different angles within a plane. A plurality, such as tens or hundreds, of receive beams are formed for each transmission. The transmit aperture is synthesized from coherent combination of the receive beams from different angles. This may increase 2-way lateral bandwidth in the long axis dimension, improving the detection of small point targets.

If an elevation lens is provided, compounding or aperture synthesis may be achieved by combining data obtained with the array at different elevation positions. Coherent or incoherent combination may not be provided along the elevation axis. The point spread function (PSF) in elevation is the product of a lens focused transmit beam and a low F-number dynamically focused receive beam based on a large (e.g., 3.5 cm) of coherent aperture in the embodiment shown in FIG. 4. In other embodiments, coherent or incoherent combination is provided for steered spatial compounded and/or to interpolate receive scan lines for increasing receive scan line density.

The detector 18 is configured to detect data output by the beamformer 14 and responsive to the moving transducer array 62. The detector 18 is an ultrasound detector. The detector is configured by hardware and/or software to detect from the beamformed and/or interpolated data. Any detection may be used, such as B-mode, Doppler or color flow mode, harmonic mode, or other now known or later developed modes. B-mode and some harmonic modes use single pulse scan techniques for detection. The intensity of the received signals in the frequency band of interest is calculated. Multiple pulse techniques, such as flow mode estimation of velocity or energy, may be used.

The detector 18 detects the response to the transmit beams for the scan of the volume. The spatial and/or temporal resolution of the detected data is based on the beamforming or scanning resolution. Detected data representing the volume is provided.

The processor 16 is a rendering processor configured by hardware and/or software. The processor 16 is a general processor, control processor, application-specific integrated circuit, field-programmable gate array, graphics processing unit, digital circuit, analog circuit, digital signal processor, combinations thereof, or other now known or later developed device for generating a three-dimensional rendering of a volume scanned with different planes. The processor 16 is a single device or group of devices. For example, the processor 16 includes separate processors operating in parallel or sequence. As another example, the processor 16 includes a network of devices for distributed processing in parallel or sequence. In one embodiment, the processor 16 is a specific device for three-dimensional image rendering, such as a graphics processing unit, graphics card, or other device for rendering.

The processor 16 uses surface rendering, projection rendering, alpha blending, texturing or other now known or later developed rendering. The data may be resampled to a regular voxel grid. Alternatively, the rendering is performed from data in a scan format, such as associated with the actual scan lines and/or interpolated scan lines. In yet other embodiments, the processor 16 is not provided or is a scan converter for generating a two-dimensional image representing a scanned plane or a reconstruction of a plane from a scanned volume.

The processor 16, the detector 18, or a separate processor generates images from the volume scan and/or plane scan or other data output from the detector 18. For example, grayscale and/or color coding is used to generate a B-mode, Doppler mode, or B-mode Doppler mode combination. Any image, such as a three-dimensional rendering, is output to the display 24.

The display 24 is a CRT, LCD, plasma, projector, printer, or other now known or later display device. The display 24 receives the image data from the processor 16 or other component and generates the image. A perfusion map, three-dimensional rendering, two-dimensional image, or other image is displayed.

The memory 22 is a tangible (non-transitory) computer readable storage medium, such as a cache, buffer, register, RAM, removable media, hard drive, optical storage device, or other computer readable storage media. The memory 22 is tangible by not being a signal, but a device. Computer readable storage media include various types of volatile and non-volatile storage media. The memory 22 is part of the imager 17, the imaging system 16, the transducer probe 12, or separate from both. The memory 22 is accessible by the processor 16 or electronics of the transducer probe 12.

In one embodiment, the memory 22 stores aperture selection and beamformer control data. The memory 22 may store data for use by the processor 16, such as storing detected and/or image data. Additionally or alternatively, the memory 22 stores data representing instructions executable by the programmed processor 16, processor of the beamformer 14, and/or processor of the probe electronics for scanning with ultrasound and/or controlling the motor 70 of the transducer probe 12. The instructions for implementing the processes, methods and/or techniques discussed herein are provided on computer-readable storage media or memories. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

FIG. 10 shows a method for medical diagnostic ultrasound imaging. The method includes acts for scanning a plurality of planes with a mechanically-translated, multi-dimensional transducer using a one-dimensional transmit array and multi-dimensional receive array. A three-dimensional volume is scanned. The method is implemented using the system of FIG. 1, the transducer probe 12 of FIG. 2, the transducer array 62 of FIG. 3 or 4, or a different system, probe or array. The method is performed in the order shown or a different order. Additional, different, or fewer acts may be provided. For example, acts 42 or 44 are not provided.

In act 37, a plurality of transmit beams are transmitted in a plane with a one-dimensional array. The beams are transmitted sequentially, but two or more beams may be transmitted simultaneously. The beams are steered at any of various angles, from any of various origination locations from the face of the array, and in any desired format. The steering is in azimuth. No electronic steering is provided in elevation, but may be. The plane is straight ahead of the one-dimensional array in elevation. A lens may focus in elevation.

The transmit beam is wide enough for parallel receive beams in both azimuth and elevation. The parallel receive beams in elevation may be for the same scan line or may be spatially adjacent beams in elevation. Alternatively, the transmit beam is wide in azimuth for receiving two or more receive beams simultaneously but just wide enough in elevation for one receive beam. The transmit beam may be converging, diverging, or a plane wave at the face of the array. In other embodiments, the transmit beam is for receiving along a single scan line.

To form the transmit beams, transmit waveforms are generated. The waveforms are generated in an imaging system separate from the one-dimensional transmit array. The transducer assembly is free of transmit waveform generators. The imaging system outputs through coaxial cable analog transmit waveforms.

The one-dimensional transmit array is a dedicated array of elements. In the fully bistatic embodiment, the elements are used just for transmission. Alternatively, the elements may be used for both transmission and reception. For example, a multi-dimensional array of elements has elements connected together by switches and/or electrode patterns to operate as a one-dimensional transmit array. Each transmit element of the transmit array is formed from one or more receive elements.

Figure 9:
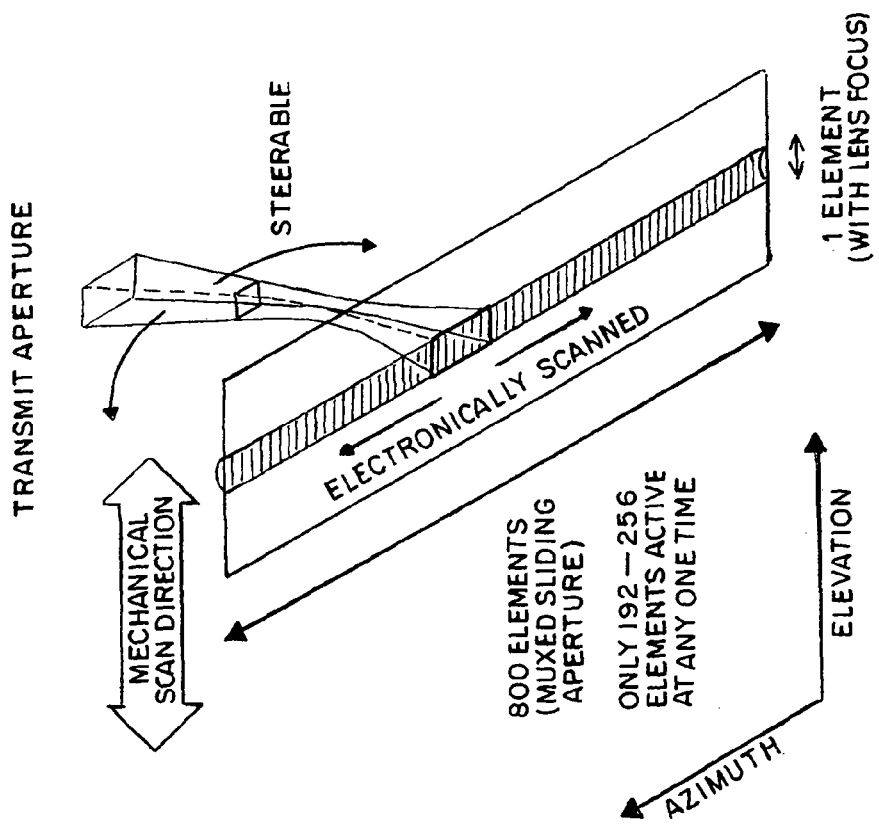
FIG. 9 is an example illustration of transmit scanning in an azimuth plane.

FIG. 9 shows an aperture being used to scan a region of a plane. The same aperture may be used to scan the entire plane or just a portion of the plane. Other apertures scan other portions, overlapping portions, or the entire plane. Since the apertures are at different locations on the array, any overlapping scan regions are from different steering directions relative to the scan location.

FIGS. 11A-C show the same location being scanned from different apertures and resulting in different angles of incidence at the location. Each aperture is at a different azimuth position on an array. The aperture may slide along an array. For example, the aperture is translated laterally or in azimuth along an array of elements.

Any step size for the translation may be used. The step size is the same between each aperture location. For example, equal amounts of translation are provided for each aperture location. Alternatively, two, three or other numbers are apertures are provided equally spaced along the array. Unequal spacing and/or aperture sizes may be used.

In act 40, receive beams are formed in response to the transmitting. The receive beams are formed by beamformation. One or more beams along different or the same scan lines are formed in response to each transmit beam. The receive beams are formed in the scan plane, such as at different locations or angles in azimuth.

The receive beams are formed with a multi-dimensional array. By steering in elevation and azimuth, greater focus is provided dynamically. The multi-dimensional array abuts the one-dimensional transmit array, but is free of connection with a transmit beamformer. The receive array is a receive only array, at least for part of the array. For example, the entire 3.5 cm×15 cm transducer array of FIG. 4 is active for reception, as represented in FIG. 10. The center strip that was used for transmit is also used for reception. The outer rows are receive only. The receive aperture is continuous, with gaps between adjacent tiles 78 kept small enough to allow coherent beamformation across the gaps. As another example, one part of the entire elevation extent of the array is used for receive. The part corresponds to the receive arrays and not the transmit array, such as using the transducer of FIG. 3. In yet another example, the receive aperture is limited in azimuth. Aperture synthesis may be used.

Echoes impinging on the elements of the current aperture are transduced to electrical energy. The electrical energy from each element of the aperture is relatively delayed and/or weighted to beamform for a given location along each scan line. Digital and/or analog dynamic beamforming may be provided. The samples may be filtered or otherwise combined, such as for imaging at a cubic fundamental or phase inversion imaging.

Any now known or later developed reception and formation of samples representing locations along one or more scan lines for each transmit event may be used. For example, fixed phase combination is provided for sub-apertures. Alternatively or additionally, dynamic partial beamforming is provided for sub-apertures. The partially beamformed data is beamformed.

A feedback is shown from act 40 to act 37. The transmitting and receiving acts 37 and 40 are repeated. The repetition if for different apertures, different scan lines or angles, or other repeats of scans of a same plane. Same is used relatively. The scan repetition occurs electronically at sufficient speed that the slower movement of the transducer and/or patient results in the same plane being scanned even if offset due to the motion.

The repetition is for spatial compounding or collecting information representing the same plane for coherent or incoherent combination. The transmit and receive beams may both be steered in azimuth. It is therefore possible to acquire multiple frames in azimuth at various angles and incoherently compound the frames together to improve detection of low contrast lesions.

In act 42, the one-dimensional transmit array and the multi-dimensional receive array are mechanically moved. A motor moves the transducer. For example, a scissor mechanism, a belt, a pulley, a gear, or an extendable rod is moved by the motor. The transducer array is attached to the mechanism, moving the transducer array along one or more guides.

The transducer array is continually moved, other than changing directions at the ends of the range of motion, while scanning. Any speed may be used. The speed is generally constant except for starting from a stopped position and breaking. Alternatively, the transducer array moves in steps, stopping for each scan.

The transducer array is moved laterally, such as along an elevation dimension in a flat plane. The movement is in a plane, but may be over a curved surface or along a curved guide. The curve may be in depth, elevation, and/or azimuth. For example, the transducer may rotate.

At different positions of the transducer during movement, planes are scanned. The feedback from act 42 to act 37 represents repeating the scanning for different positions of the transducer and corresponding positions of the scan planes. The difference in position may cause the elevation focal regions to overlap or may be non-overlapping.

By scanning different planes, a volume is scanned. The volume is acquired by using electronic scanning to capture an entire frame in azimuth, and mechanically translating by a small amount in elevation prior to acquisition of the next frame. For the volume scan, the three-dimensional volume is scanned with ultrasound sequentially.

In act 44, data from different repetitions of scans in the same plane are coherently or incoherently combined. For example, spatial steered compounding for each scan plane is provided by compounding detected data representing the same locations but from different angles. As another example, aperture synthesis is performed by compounding beamformed, coherent data representing the same locations.

The combinations are performed for the azimuth data representing the same plane. In an alternative embodiment, data for the same plane is acquired from elevation spaced receive arrays. The data may be combined coherently or incoherently.

The combination is performed for each of the scan planes of the volume scan. For each repetition of the transmission, reception, and movement acts, the combination is performed. Alternatively, no combination is provided for one or more planes.

In act 50, an image is generated from the acquired data. The received data and/or the interpolated data are detected. Any detection process may be used. For example, the intensity of the return is detected as B-mode data. As another example, the energy (power), velocity, and/or variance of moving tissue or fluid are detected as Doppler data. Contrast agent, harmonic, or other types of detection may be provided.

Some types of detection use a plurality of samples for each spatial location. The scanning for a given aperture location is performed multiple times to acquire the data for the detection. The repetition is performed before scanning with a different aperture and/or for a different scan line. Alternatively, the sampling for detection may be interleaved with other scans.

An image is generated from the detected data. The data received by scanning is used to generate the image. The image represents a volume, plane or line. For two-dimensional imaging, the data may be scan converted and mapped to display values. For example, B-mode information is mapped to a gray scale and Doppler data is mapped to a color scale.

For a volume, the image is rendered from the data representing the volume. Any now known or later developed rendering may be used. For example, surface rendering or projection rendering are performed. The image is rendered as a three-dimensional representation from data for the various scan planes. Alternatively, the data from the scan planes is interpolated to a regular grid, and the image is rendered from the grid data. Shading and/or opacity weighting may be used. The data may be filtered before or after image generation.

The generation of the image occurs in real-time with the scanning. For example, the image is generated while still scanning to acquire data for subsequent images. The image is generated in a same imaging session as the acquisition. The processing delay between scanning and generating the image may be a few seconds or less, such as less than one second. The volume is scanned a plurality of times each second. The images are generated at the scan rate in a short time to allow processing after completion of corresponding scans of the entire volume. In other embodiments, the data is stored. The image generation occurs from the stored data rather than being in real-time with the scanning.

While the invention has been described above by reference to various embodiments, it should be understood that many changes and modifications can be made without departing from the scope of the invention. The above embodiments are examples. It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A transducer array for medical diagnostic ultrasound imaging, the transducer array comprising:
    a one-dimensional transducer array configured for transmit only operation or transmit and receive operation, the one-dimensional transducer array having, for transmit operation, a plurality of transmit elements distributed along an azimuth dimension with only a single row of the elements in an elevation dimension;
    a multi-dimensional transducer array adjacent an elevation edge of the one-dimensional transducer array, the multi-dimensional transducer array configured for receive only operation, the multi-dimensional transducer array having N×M receive elements distributed along the azimuth and elevation dimensions where N and M are both greater than one; and
    a motor configured to move the one-dimensional and multi-dimensional transducer array together along the elevation direction.

2. The transducer array of claim 1 wherein the one-dimensional and multi-dimensional transducer arrays are co-located;
    further comprising a guide in which the co-located one-dimensional and multi-dimensional transducer arrays are connected together and translate due to force applied by the motor.

3. The transducer array of claim 1 wherein the one-dimensional transducer array is a transmit only array.

4. The transducer array of claim 1 wherein the one-dimensional transducer array comprises first elements distributed along the azimuth and elevation dimensions, the first elements each having top and bottom electrodes and being individually accessed electrically with the bottom electrodes for the receive operation, the top electrodes extending across columns of the first elements in elevation to form the transmit elements for transmit operation, each transmit element comprising a plurality of receive elements.

5. The transducer array of claim 1 further comprising:
a probe housing; and
partial beamforming circuits in the probe housing with the multi-dimensional transducer array, the partial beamformer circuits connected with the receive elements.

6. The transducer array of claim 1 further comprising connections with the transmit elements configured to connect with a beamformer of the imaging system without transmit electronics in a housing of the transducer array.

7. The transducer array of claim 1 wherein the multi-dimensional transducer array comprises a cMUT array monolithically integrated above electronics configured to reduce a number of signals from N×M signals by at least half through combination of the signals.

8. The transducer array of claim 1 further comprising an additional multi-dimensional transducer array adjacent an another elevation edge of the one-dimensional transducer array opposite the elevation edge, the additional multi-dimensional transducer array configured for receive only operation, the additional multi-dimensional transducer array having additional receive elements distributed along the azimuth and elevation dimensions.

9. The transducer array of claim 1 further comprising a multiplexer, the multiplexer configured to select an aperture comprising a sub-set of the transmit and receive elements along the azimuth dimension.

10. The transducer array of claim 1 wherein the transmit elements comprise piezoelectric elements.

11. The transducer array of claim 1 wherein the receive and transmit elements are spaced along at least ten centimeters in the azimuth dimension, the receive elements grouped into separate tiles abutting each other.

12. An ultrasound system for medical diagnostic ultrasound imaging, the system comprising:
a transducer array comprising a two-dimensional transducer array having a first row of elements configured for transmit operation, the first row of elements distributed along an azimuth dimension with only a single row of the elements in an elevation dimension, and at least second and third rows of elements configured for receive only operation, the second and third rows of elements each abutting an elevation edge of the first row of elements;
a guide arranged to translate the transducer array generally perpendicular to the first row; and
a beamformer configured to transmit acoustic energy with the first row of elements and receive echo signals with the second and third rows of elements, repeated with the transducer array at different positions along the guide such that a volume is scanned,
wherein the second and third rows of receive elements are each a multi-dimensional transducer array having N×M receive elements distributed along the azimuth and elevation dimensions where N and M are both greater than one.

13. The ultrasound system of claim 12 wherein the first row of elements comprises a one-dimensional array of transmit elements formed from a multi-dimensional array of receive elements, the elements of the second and third rows being a same size as the receive elements, and each of the transmit elements having a length in elevation based on a plurality of the receive elements combined together.

14. The ultrasound system of claim 12 wherein the first row of elements comprises a one-dimensional array of piezoelectric elements and second and third rows of elements comprise cMUT elements.

15. The ultrasound system of claim 12 wherein the beamformer comprises a transmit beamformer in an imaging system releasably connectable with the transducer array and a receive beamformer having a partial beamformer at the transducer array and a system beamformer in the imaging system, the system beamformer configured to beamform from partially beamformed signals output by the partial beamformer.

16. The ultrasound system of claim 12 wherein the beamformer is configured to scan a plurality of planes, each plane being at one of the different positions of the transducer array in the guide;
further comprising a coherent or incoherent combiner configured to combine different scans from a same one of the planes.

17. A method for medical diagnostic ultrasound imaging, the method comprising:
transmitting a plurality of transmit beams in a plane with a one-dimensional array;
receiving, in response to the transmitting, receive beams in the plane with a multi-dimensional array having N×M receive elements distributed along azimuth and elevation dimensions where N and M are both greater than one, the multi-dimensional array abutting the one-dimensional array along an elevation edge and being free of connection with a transmit beamformer;
mechanically moving the one-dimensional array and the multi-dimensional array; and
repeating the transmitting and receiving at different positions of the one and multi-dimensional arrays.

18. The method of claim 17 wherein transmitting comprises generating the transmit waveforms in an imaging system separate from a transducer assembly of the one-dimensional array, the transducer assembly free of transmit waveform generators.

19. The method of claim 17 wherein transmitting comprises transmitting with the one-dimensional array of transmit elements each formed from a plurality of receive elements, and wherein receiving comprises receiving with the multi-dimensional array and the receive elements.

20. The method of claim 17 wherein the transmitting and receiving are repeated at each of the different positions; and
further comprising coherently or incoherently combining data from each of the repetitions for each different position.

* * * * *